United States Patent
Becker et al.

(10) Patent No.: US 6,602,476 B2
(45) Date of Patent: Aug. 5, 2003

(54) APPARATUS AND PROCESS FOR HEAT EXCHANGE WITH FLUID BEDS

(75) Inventors: Stanley John Becker, Addlestone (GB); Timothy Crispin Bristow, Beverley (GB); Michele Fiorentino, Aix en Provence (FR); David Newton, Farnham (GB); Bruce Leo Williams, Brough (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/964,881

(22) Filed: Sep. 28, 2001

(65) Prior Publication Data
US 2002/0074107 A1 Jun. 20, 2002

(30) Foreign Application Priority Data
Oct. 26, 2000 (GB) .............................................. 0026242

(51) Int. Cl.[7] .......................... F27B 15/14; F27B 15/08; C07D 307/36; B01J 20/34; C07C 67/00
(52) U.S. Cl. ....................... 422/146; 422/145; 422/143; 208/159; 502/41; 502/51; 549/762; 558/308; 558/330; 558/435; 560/232; 560/241.1; 560/242; 560/261; 562/521; 562/548; 562/549; 562/607
(58) Field of Search ........................... 549/262; 422/145, 422/146, 143; 208/159; 502/41, 51; 558/308, 330, 435; 560/241.1, 232, 247, 261; 562/521, 548, 549, 607

(56) References Cited

FOREIGN PATENT DOCUMENTS

| EP | 0 546 677 A1 | 6/1993 |
|----|--------------|--------|
| EP | 0 672 453 A2 | 9/1995 |
| EP | 0 776 692 A1 | 6/1997 |
| EP | 0 847 982 A1 | 6/1998 |
| EP | 1 034 837 A2 | 9/2000 |
| EP | 1 034 838 A2 | 9/2000 |
| EP | 1 043 064 A2 | 10/2000 |
| WO | 88/51339 | 10/1999 |

*Primary Examiner*—Alan L. Rotman
*Assistant Examiner*—Raymond Covington
(74) *Attorney, Agent, or Firm*—Nixon & Vanderhye

(57) ABSTRACT

Apparatus and process for heat exchange with fluid beds comprises heat-exchange tubes located longitudinally with respect to the axis of a fluidization zone with a rectangular pitch, one side of which having a length at least one and a half times the length of the other side and/or with a triangular pitch, having two sides each at least one and a half times the length of the shortest side reduces the impact of the heat-exchange tubes on the fluidization characteristics of the fluid bed. The invention is particularly suitable for oxidation reactions using molecular oxygen-containing gas in the presence of a fluid bed of fluidizable catalyst, such as (a) the acetoxylation of olefins, (b) the oxidation of ethylene to acetic acid and/or the oxidation of ethane to ethylene and/or acetic acid, (c) the ammoxidation of propylene and/or propane to acrylonitrile and (d) the oxidation of C4's to maleic anhydride.

41 Claims, 2 Drawing Sheets

APPARATUS AND PROCESS FOR HEAT EXCHANGE WITH FLUID BEDS

Figure 1:
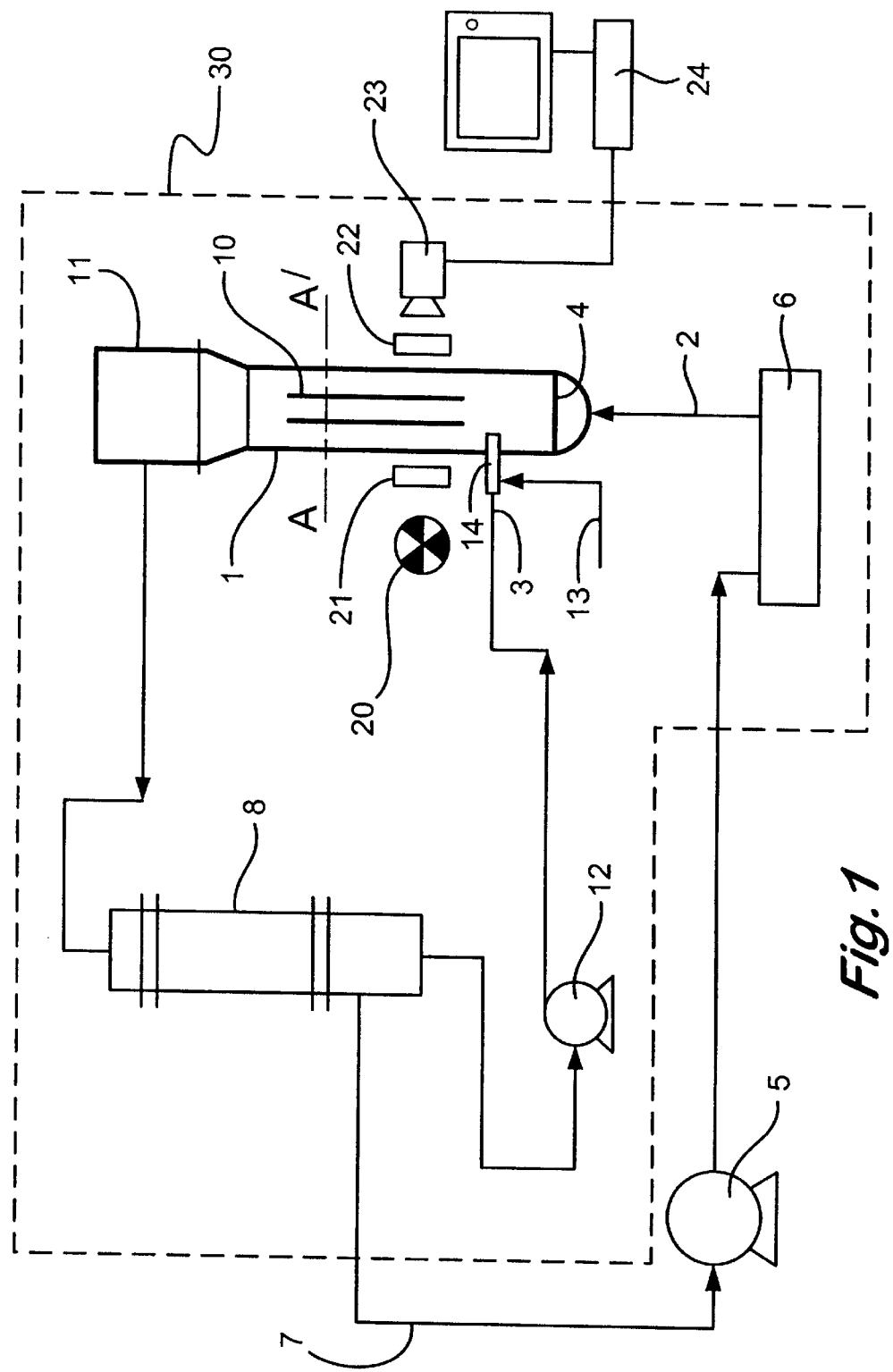

The present invention relates in general to apparatus and process for heat exchange with fluidised beds of material.

BACKGROUND OF THE INVENTION

Fluid bed reactors and their use in processes involving heterogeneous gas-phase reaction which are exothermic are known, for example from EP-A-0546677, EP-A-0685449 and EP-A-0847982.

EP-A-0546677 discloses a process for oxidising ethane to acetic acid in a fluidized bed reaction zone. In the example illustrated in EP-A-0546677, ethane is joined with a recycle stream containing water, CO, $CO_2$, $O_2$, ethylene and ethane and the combined stream is fed to the fluid bed reactor. A molecular oxygen-containing stream and steam are introduced separately into the fluid bed reactor. The hot oxidation products exit the top of the reactor and flow through a steam generator heat-exchanger, coolers and an air cooler. The fluidised bed reactor is also said to contain cooling coils (not shown) in the bed into which water is introduced and from which steam exits.

EP-A-0685449 discloses a process for manufacturing vinyl acetate in a fluid bed reactor comprising feeding ethylene and acetic acid into the fluid bed reactor through one or more inlets, feeding an oxygen-containing gas into the fluid bed reactor through at least one further inlet, co-joining the oxygen-containing gas, ethylene and acetic acid in the fluid bed reactor while in contact with a fluid bed catalyst material to enable the ethylene, acetic acid and oxygen to react to produce vinyl acetate and recovering the vinyl acetate from the fluid bed reactor. EP-A-0685449 describes the use of a fluid bed reactor containing a fluidisable microspheroidal catalyst which is equipped with cooling coils which provide for heat transfer from the reactor.

EP-A-0847982 discloses a process for the production of vinyl acetate by reacting at elevated temperature in a fluid bed reactor ethylene, acetic acid and an oxygen-containing gas in the presence of a fluid bed catalyst material characterised in that a liquid is introduced into the fluidised reactor for the purpose of removing heat therefrom by evaporation of the liquid.

Heat-exchange tubes in a fluid bed reactor may be used to remove heat of an exothermic reaction. They may also be used for heating the bed of fluidisable catalyst or even drying the catalyst, for example following a shutdown.

According to EP-A-0847982, it is desirable to use some cooling tubes/coils to provide "fine tuning" of the heat removal. According to EP-A-0847982, typically, about 70% of the heat removal may be provided by liquid addition to the reactor. It is further stated that any appropriate percentage between 100 and greater than 0% of the heat removal may be by means of liquid additions to the reactor without exceeding the safety margins of the equipment operated.

EP-A-0776692 describes the use of heat exchange elements in a fluid bed reactor, in which means for supporting one or more essentially horizontal support beams is achieved by replacing a continuous ledge with a discontinuous support structure.

EP-A-1034837 relates to the use of a fluid bed reactor containing cooling tubes for oxychlorination of ethylene to produce vinyl chloride monomer. The cooling tubes are spaced equidistant relative to each other and may be arranged in a square (90°) and/or triangular (60°) configuration.

A problem with the use of heat-exchange tubes in fluid beds is that they may interfere with the fluidisation characteristics of the fluid bed. This problem is particularly significant in very exothermic fluid bed reactions, requiring a large number of heat-exchange tubes. The problem to be solved therefore is to provide an apparatus for use with fluid beds in which the impact of the heat-exchange tubes on the fluidisation characteristics of the fluid bed is reduced whilst retaining heat exchange capacity. It has been found that this can be achieved by using a defined arrangement of heat-exchange tubes.

SUMMARY OF THE INVENTION

Thus, according to one embodiment of the present invention there is provided apparatus comprising a vessel having:
(1) means for fluidising a bed of fluidisable material within a fluidisation zone in the vessel; and
(2) heat-exchange tubes located in the fluidisation zone for removing heat from the fluidisation zone and/or for providing heat to the fluidisation zone,
characterised in that the heat-exchange tubes are located longitudinally with respect to the axis of the fluidisation zone with a rectangular pitch, one side of which having a length at least one and a half times the length of the other side and/or with a triangular pitch, having two sides each at least one and a half times the length of the shortest side.

According to another aspect of the present invention there is provided a process for removing heat from a fluidised bed of material and/or supplying heat to a fluidised bed of material which process comprises
(i) fluidising a bed of fluidisable material within a fluidisation zone in a vessel having means for supporting the fluidised bed of material; and
(ii) removing heat from the fluidised bed of material and/or providing heat to the fluidised bed of material, by heat-exchange tubes located in the fluidisation zone longitudinally with respect to the axis of the fluidisation zone with a rectangular pitch, one side of which having a length at least one and a half times the length of the other side and/or with a triangular pitch, having two sides each at least one and a half times the length of the shortest side.

The present invention solves the technical problem defined above by using heat-exchange tubes located in a rectangular pitch, one side of which having a length at least one and a half times the length of the other side and/or in a triangular pitch, having two sides each at least one and a half times the length of the shortest side.

It has been found that this arrangement allows for a large number of heat-exchange tubes to be located in the fluidisation zone without significantly interfering with the fluidisation characteristics of the fluid bed of material.

The rectangular pitch of the heat-exchange tubes has sides of length x and y in which x is at least one and a half times y, preferably at least 2.5 times y. The triangular pitch arrangement has two sides each of which is at least one and a half times the length of the shortest side, preferably 2.5 times the length of the shortest side.

It is important that the heat-exchange tubes are not too close together—that is, for the rectangular pitch the value of y should not be too small and for the triangular pitch the shortest side should not be too small to be ineffective. For example, for tubes of 50 mm diameter a minimum distance between tubes of 25 mm corresponding to a minimum distance of 75 mm centre to centre, is appropriate.

Other parameters may also have an impact on the fluidisation characteristics of the bed of fluidised material. For example, the heat-exchange tube diameter, the proportion of cross-sectional area of the vessel occupied by the heat-exchange tubes and the degree of compactness of the heat exchange tubes (Φ) which is the tube cross sectional area divided by the pitch area.

It has now been found that for heat removal from a fluidisation zone using heat exchange tubes, the heat exchange tubes should be operated at a temperature of not less than the dew point of the fluid in the fluidisation zone and preferably at a temperature of at least 10° C. above the dew point of the fluid in the fluidisation zone.

Thus, according to another aspect of the present invention there is provide a method for heat removal from a fluidisation zone by using heat exchange tubes in which the heat exchange tubes are operated at a temperature of not less than the dew point of the fluid in the fluidisation zone and preferably at a temperature of at least 10° C. above the dew point of the fluid in the fluidisation zone.

For removing heat from the fluidised bed of material in the fluidisation zone, the heat-exchange tubes are supplied with a cooling fluid such as water. The present invention is particularly advantageous when the temperature of the cooling tubes has to be restricted to avoid excessive cold spots and/or surfaces in the fluidisation zone. For example, the temperature of the cooling tubes is preferably 10 to 15° C. greater than the dew point of the fluid in the fluidisation zone. In such situations, the number of heat-exchange tubes has to be relatively large in order for sufficient heat to be removed. The impact of this large number of heat-exchange tubes on the fluidisation characteristics of the fluidised bed is reduced by the present invention. Thus, for example in the acetoxylation of ethylene with acetic acid and oxygen, the temperature of the cooling tubes should be no less than 110° C. and is preferably should be at least 120° C. Operating with a cooling tube at a temperature above the dew point of the mixture of reagents in the reactor helps prevent condensation of liquid on the heat-exchange tubes which can adversely affect the fluidised bed of catalyst.

For supplying heat to the fluidised bed of material in the fluidisation zone, the heat-exchange tubes are provided with a heating fluid such as steam, hot water or other hot process fluids.

The present invention is particularly suited for heterogeneous gas-phase reactions in the presence of a fluidised bed of fluidisable catalyst, and in particular exothermic reactions in which at least a part of the heat of reaction is removed by the heat-exchange tubes.

The present invention is particularly suitable for oxidation reactions in which at least one reactant is brought into contact with a molecular oxygen-containing gas in the presence of a fluid bed of fluidisable catalyst, including for example (a) the acetoxylation of olefins, for example the reaction of ethylene, acetic acid and oxygen to produce vinyl acetate, (b) the oxidation of ethylene to acetic acid and/or the oxidation of ethane to ethylene and/or acetic acid, (c) the ammoxidation of propylene, propane or mixtures thereof to acrylonitrile and (d) the oxidation of C4's to maleic anhydride, although it may be used in other fluid bed processes requiring heat-exchangers.

Preferably, the apparatus and process of the present invention are used for the acetoxylation of ethylene to produce vinyl acetate because this reaction is very exothermic and a fluid bed reactor can be used to provide good temperature control.

Thus, according to another aspect of the present invention there is provided apparatus for reacting at least one reactant with molecular oxygen-containing gas in the presence of a fluidised bed of catalyst which apparatus comprises a reactor having:

(a) means for fluidising a bed of fluidisable catalyst within a fluidisation zone in the reactor;
(b) means for introducing at least one reactant into the reactor;
(c) means for introducing a molecular oxygen-containing gas into a fluidised bed of catalyst in the fluidisation zone in the reactor and contacting the at least one reactant with the molecular oxygen-containing gas in the presence of the fluidised bed of catalyst in the fluidisation zone; and
(d) heat-exchange tubes located in the fluidisation zone longitudinally with respect to the axis of the fluidisation zone with a rectangular pitch, one side of which having a length at least one and a half times the length of the other side and/or with a triangular pitch, having two sides each at least one and a half times the length of the shortest side.

Also, according to another aspect of the present invention there is provided a process for reacting at least one reactant with molecular oxygen-containing gas in the presence of a fluidised bed of catalyst which process comprises:

(a) fluidising a bed of fluidisable catalyst within a fluidisation zone in a reactor having means for supporting the fluidised bed of catalyst;
(b) introducing at least one reactant into the reactor;
(c) introducing a molecular oxygen-containing gas into the fluidised bed of catalyst in the fluidisation zone in the reactor;
(d) contacting the at least one reactant with the molecular oxygen-containing gas in the presence of the fluidised bed of catalyst in the fluidisation zone; and
(e) removing at least part of the heat of reaction from the fluidisation zone by heat-exchange tubes located in the fluidisation zone longitudinally with respect to the axis of the fluidisation zone with a rectangular pitch, one side of which having a length at least one and a half times the length of the other side and/or with a triangular pitch, having two sides each at least one and a half times the length of the shortest side.

In addition to the heat-exchange tubes, at least a part of the heat of reaction may be removed from the reactor by introducing to the reactor cold gas, such as feed and/or recycle gas and removing from the reactor hot gas such as reaction product and/or unconsumed reactants; the unconsumed reactants being cooled outside the reactor and recycled to the reactor.

Liquid may be introduced into the reactor as reactant and/or for the purpose of removing heat therefrom by evaporation of the liquid. Thus, means may be provided for introducing liquid into the reactor as reactant and/or for the purpose of removing heat therefrom by evaporation of the liquid. The liquid introduced into the fluidised bed of catalyst may suitably be a reactant, an inert liquid or a product of the reaction, or a mixture of any two or more thereof In the acetoxylation of ethylene with a molecular oxygen containing gas and acetic acid, for example, the acetic acid reactant may be fed to the fluidised bed of catalyst in liquid form; a suitable product which may be introduced into the fluidised bed of catalyst is water, which is formed as a by-product of the acetoxylation reaction and has a relatively high latent heat of evaporation; and vinyl acetate product and/or acetaldehyde by-product may also be recycled and introduced in liquid form into the fluidised bed of catalyst.

Preferably, any inlet for liquid is positioned such that the liquid does not impinge on any cooler surfaces (other than those of the fluid bed of fluidised material) within the fluidisation zone, such as the surface of heat-exchange tubes located within the fluidisation zone to remove heat of reaction.

For example, in the acetoxylation of ethylene to produce vinyl acetate, about 30 to 40% of the heat of reaction may be removed by liquid addition to the reactor, about 30 to 40% of the heat of reaction may be removed by recycle of cooled gases and about 30 to 40% of the heat of reaction may be removed by the heat-exchange tubes. However, any appropriate proportion up to 100%, preferably less than 100%, of the heat removal may be by means of the heat-exchange tubes.

The heat-exchange tubes may be used for heating up the fluid bed reactor at start-up, by passing a suitable fluid at elevated temperature through the tubes. Once the reactor is at the required temperature the fluid at elevated temperature may be replaced by cooling fluid.

The heat-exchange tubes may also be used for drying the catalyst, for example following a shutdown.

The reactor according to the present invention may have one or more inlets for molecular oxygen-containing gas. The molecular oxygen-containing gas for these inlets may be provided from a common source such as a common end box. Molecular oxygen-containing gas and other gases may also be introduced to the reactor by other inlets, for example as components in recycle gases and/or mixed feed gases.

Any suitable inlet for the reactants may be used in the present invention, in particular recognising the hazards which may have to be considered with such reactants. Thus, for example, for a molecular oxygen-containing gas, for safety, it is preferably located at a distance from the catalyst support means of greater than any potential flame length.

Inlets for molecular oxygen-containing gas may comprise means for safe introduction of this potentially hazardous material.

Suitable molecular oxygen-containing gases for use in the present invention include air, oxygen-enriched air and oxygen gas with minor amounts of impurities such as nitrogen, carbon dioxide, argon etc. Thus, there may be used oxygen gas which is 99.6% by vol. pure with impurities such as argon, preferably not greater than 0.4% by volume, typically <0.1% by volume. The concentration of nitrogen is preferably <0.1% by volume. The concentration of oxygen in the molecular oxygen-containing gas is suitably in the range from 10 to 100% by volume, preferably in the range from 30 to 100% by volume.

The reactor according to the present invention may have one or more inlets for at least one reactant which may be introduced into the reactor optionally with recycle gases below the support means to fluidise the bed of catalyst. The at least one reactant introduced into the reactor may be a gas, for example (i) ethylene and/or (ii) ethane which may be reacted with the molecular oxygen-containing gas to produce respectively (i) acetic acid and/or (ii) ethylene and/or acetic acid. Ethylene may also be used with molecular oxygen-containing gas and acetic acid to produce vinyl acetate. Ethylene and/or ethane in these reactions may be used in substantially pure form or admixed with one or more of nitrogen, methane, ethane, carbon dioxide and water in the form of steam or one or more of hydrogen, $C_3/C_4$ alkenes or alkanes.

The reactor and processes of the present invention may suitably be used at a temperature from 50 to 1500° C., preferably 100 to 1000° C. The reactor of the present invention may be operated at a pressure of from 10 to 10000 kPa gauge (from 0.1 to 100 barg), preferably from 20 to 5000 kPa gauge (from 0.2 to 50 barg).

In the fluidisation zone of the vessel, the particles of the material are maintained in a fluidized state by suitable gas flow through the bed of material. Excess flow rate in a fluid bed with cooling coils may cause channelling of the gas through the bed of material and in a reactor with a fluidised bed of catalyst this may decrease heat removal and conversion efficiency.

The fluidisable material may be any suitable fluidisable catalyst. The catalyst may be a supported catalyst. Suitable catalyst supports include porous silica, alumina, silica/alumina, titania, silica/titania, zirconia and mixtures thereof. Preferably, the support is silica. Suitably, the support may have a pore volume from 0.2 to 3.5 mL per gram of support, a surface area of 5 to 800 $m^2$ per gram of support and an apparent bulk density of 0.3 to 5.0 g/ml.

A typical catalyst composition useful in this invention, may have the following the particle size distribution:

| | |
|---|---|
| 0 to 20 microns | 0–30 wt % |
| 20 to 44 microns | 0–60 wt % |
| 44 to 88 microns | 10–80 wt % |
| 88 to 106 microns | 0–80 wt % |
| >106 microns | 0–40 wt % |
| >300 microns | 0–5 wt % |

Persons skilled in the art will recognise that support particles sizes of 44, 88, 106 and 300 microns are arbitrary measures in that they are based on standard sieve sizes. Particle sizes and particle size distributions may be measured by an automated laser device such as a Microtrac X100.

Suitably, the catalyst has a bulk density of from 0.5 to 5 $g/cm^3$, preferably 0.5 to 3 $g/cm^3$, especially 0.5 to 2 $g/cm^3$.

Suitable catalysts for use in the present invention include oxidation, ammoxidation and acetoxylation catalysts.

A catalyst suitable for use in the production of vinyl acetate by the acetoxylation of ethylene may comprise a Group VIII metal, a catalyst promoter and an optional co-promoter. The catalyst may be prepared by any suitable method, such as that described in EP-A-0672453, the contents of which are hereby incorporated by reference. The Group VIII metal is preferably palladium. The Group VIII metal may be present in a concentration of greater than 0.2% by weight, preferably greater than 0.5% by weight based upon total weight of catalyst. The metal concentration may be as high as 10% by weight. Suitable promoters include gold, copper, cerium or mixtures thereof. A preferred promoter is gold. The promoter metal may be present in an amount of from 0.1 to 10% by weight in the finished catalyst. Suitable co-promoters include Group I, Group II, lanthanide or transition metals, for example selected from the group consisting of cadmium, barium, potassium, sodium, manganese, antimony, lanthanum and mixtures thereof, which are present in the finished catalyst as salts, e.g. an acetate salt. The preferred salts are potassium or sodium acetate. The co-promoter is preferably present in the catalyst composition in a concentration of 0.1 to 15% by weight of catalyst, more preferably, from 1 to 5% by weight. When a liquid acetic acid feed is used, the preferred concentration of co-promoter salt is up to 6% by weight, especially 2.5 to 5.5%.

A suitable catalyst for the oxidation of ethane and/or ethylene is described for example in EP-A-1069945, the contents of which are hereby incorporated by reference, which describes a catalyst composition for the selective oxidation of ethane and/or ethylene to acetic acid which composition comprises in combination with oxygen the elements: $Mo_a.W_b.Ag_c.Ir_d.X_e.Y_f$ (I) wherein X is the elements Nb and V; Y is one or more elements selected from the group consisting of: Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, T, U, Re and Pd; a, b, c, d, e and f represent the gram atom ratios of the elements such that $0<a\leq1$, $0\leq b<1$ and $a+b=1$; $0<(c+d)\leq0.1$; $0<e\leq2$; and $0\leq f\leq2$.

Another suitable catalyst for the oxidation of ethane and/or ethylene is described for example in EP-A-1043064, the contents of which are hereby incorporated by reference, which describes a catalyst composition and its use for the oxidation of ethane to ethylene and/or acetic acid and/or for the oxidation of ethylene to acetic acid which comprises in combination with oxygen the elements molybdenum, vanadium, niobium and gold in the absence of palladium according to the empirical formula: $Mo_aW_bAu_cV_dNb_eY_f$(I) wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te, La and Pd; a, b, c, d, e and f represent the gram atom ratios of the elements such that: $0<a\leq1$; $0\leq b<1$ and $a+b=1$; $10^{-5}<c\leq0.02$; $0<d\leq2$; $0<e\leq1$; and $0\leq f\leq2$.

BRIEF DESCRIPTION OF THE INVENTION

Figure 2:
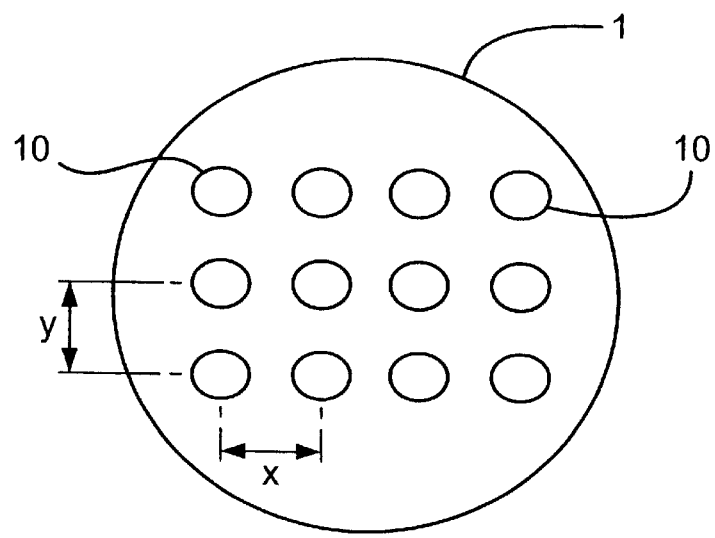
Figure 3:
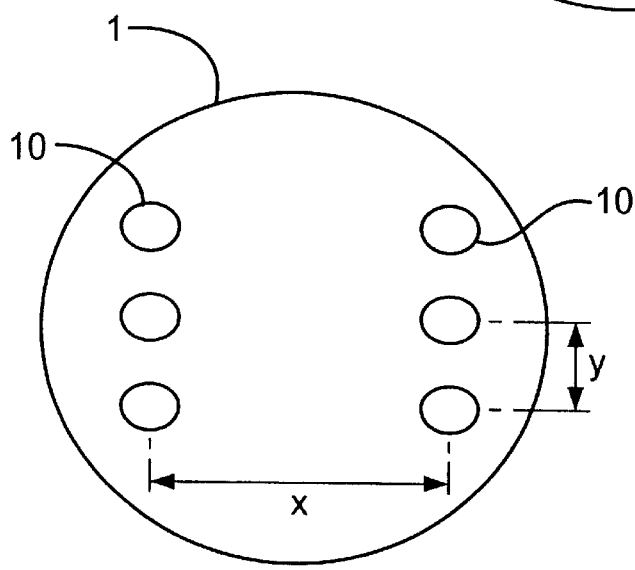
Figure 4:
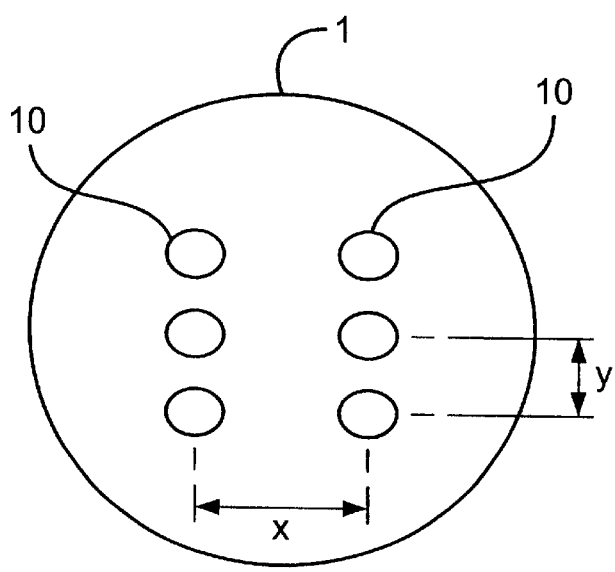

The invention will now be illustrated by way of example only and with reference to the drawings in which FIG. 1 represents schematically apparatus used for determining the fluidisation characteristics of different heat-exchange tube configurations and FIGS. 2 to 4 represent transverse cross-sections along line A–A' of the fluid bed vessel of FIG. 1 of different heat-exchange tube configurations tested with the apparatus of FIG. 1.

DETAILED DESCRIPTION OF THE PREFFERRED EMBODIMENTS a) Preparation of Catalyst Support A catalyst support for use in the catalyst preparation was prepared by spray-drying a mixture of Nalco (Nalco Chemical Company) silica sol 1060 and Degussa (Degussa Chemical Company) Aerosil® silica. In the dried support, 80% of the silica came from the sol and 20% of the silica came from the Aerosil. The spray-dried microspheres were calcined in air at 640° C. for 4 hours. This method of support preparation is described in EP-A-0672 453.

The particle size distribution of the support which was used for the subsequent catalyst preparation is given in Table 1 as follows:

TABLE 1

| Particle size | % |
| --- | --- |
| >300 microns | 2 |
| 88–300 microns | 30 |
| 44–88 microns | 38 |
| <44 microns | 30 | b) Preparation of Fluidisable Catalyst Material.

Silica support prepared as above (54.4 parts) was impregnated with a solution of $Na_2PdCl_4.xH_2O$ (containing 1 part palladium) and $HAuCl_4.xH_2O$ (containing 0.4 parts gold) in distilled water by incipient wetness. The resulting mixture was mixed thoroughly, left to stand for 1 hour and dried overnight.

The impregnated material was added slowly to a 5% solution of hydrazine in distilled water, and the mixture allowed to stand overnight with occasional stirring. Thereafter the mixture was filtered and washed with 4×400 parts distilled water. The solid was then dried overnight.

The material was impregnated with an aqueous solution of potassium acetate (2.8 parts) by incipient wetness. The resulting mixture was mixed thoroughly, left to stand 1 hour and dried overnight.

The resulting catalyst comprised 1.6 wt % Palladium, 0.6 wt % gold and 5 wt % potassium acetate. The catalyst was classified to give the following particle size distribution:

TABLE 2

| Particle size | % |
| --- | --- |
| <48 microns | 26% |
| 48–104 microns | 42% |
| >104 microns | 32% |

Using the catalyst prepared above, the performance of various configurations of heat-exchange tubes in a fluid bed vessel were studied using x-ray apparatus shown schematically in FIG. 1.

The apparatus used for the experiments comprised a 420 mm ID aluminium vessel (1), provided with a fluidising supply (2) of nitrogen gas and liquid feed system (3) in a lead-lined cell (30). The vessel (1) was provided with a distributor grid plate (4) for supporting the bed of fluidisable catalyst. The vessel was connected to a positive displacement gas re-circulation pump (5), heater (6) and gas metering/measuring system (not shown) in a pressurised closed loop (7) containing a condenser (8).

1.5 inch nominal bore (1.9 inch OD) aluminium tubes (10) were positioned within the vessel (1) to represent heat exchange tubes within a reactor. A freeboard section (11) optionally containing a cyclone was provided to disengage the catalyst.

The liquid feed system comprised a pump (12) for recycling acetic acid and a supply of nitrogen (13) to a twin fluid nozzle (14).

For the x-ray imaging, a pulsed (50 Hz) high energy beam (50–180 kV) was produced from a rotating anode (20) and was passed through a collimator (21) which was synchronised with a video camera (23) also operating at 50 Hz. During each 20 millisecond period, the collimator allowed one X-ray pulse, controllable in duration from 1–10 milliseconds, through the fluidised bed where X-ray absorption occurs proportional to the amount of material along the path. The resulting image produced on the image intensifier (22) was recorded using the video camera and video tape recorder (24). The short X-ray pulse provides a frozen image of the material within the bed, which may be followed with time.

X-Ray Experiments.

Approximately 100 kg of catalyst was loaded into the aluminium vessel and fluidised with nitrogen.

Three different heat-exchange tube configurations were tested over a range of operating conditions (temperature, pressure, fluidising velocity and with/without addition of liquid acetic acid). Once the fluid bed had stabilised at a set of conditions, an X-ray scan was made from the grid up to the bed surface. The fluidisation behaviour of the catalyst was then noted, particularly in the region of the heat exchange tubes.

Experiment 1 (comparison)

The configuration for this experiment was a 4 inch square pitch (FIG. 2): 1.9 inch OD tubes spaced apart by 2.1 inches (4 inches centre/centre) Thus, x=y=4 inches. Gas velocities between 5 and 32 cm/s, temperatures between 70 and 190° C. and pressures up to 9 bara were employed. Poor fluidisation, detected as slugging, was observed.

Experiment 2

The configuration for this experiment was a 12 inch×4 inch rectangular pitch (x:y) (FIG. 3). Gas velocities between 8 and 22 cm/s, temperatures between 50 and 60° C. and a pressure of 9 bara were employed. Very good fluidisation was observed with no slugging.

Experiment 3

The configuration for this experiment was a 8 inch×3 inch rectangular pitch (x:y) (FIG. 4). Gas velocities between 9 and 40 cm/s, temperatures between 50 and 150° C. and pressures of up to 9 bara were employed. Very good fluidisation was observed with no slugging.

The results are summarised in Table 3.

The experiments show that the heat-exchange tubes do not have an adverse effect on the fluid bed when x is greater than one and a half times b. This is even the case when the closest distance between the tubes, as in Experiment 3, is less than that in the square pitch arrangement of Experiment 1.

TABLE 3

| | Distance x between tube centres (inches) | Distance y between tube centres (inches) | Tube separation along x axis (inches) | Tube separation along y axis (inches) | Degree of compactness, $\Phi$ | Fluidisation Behaviour |
|---|---|---|---|---|---|---|
| Experiment 1 | 4 | 4 | 2.1 | 2.1 | 0.177 | Poor |
| Experiment 2 | 12 | 4 | 10.1 | 2.1 | 0.059 | Good |
| Experiment 3 | 8 | 3 | 6.1 | 1.1 | 0.118 | Good |

We claim:

1. Apparatus comprising a vessel having:

(1) means for fluidising a bed of fluidisable material within a fluidisation zone in the vessel; and (2) heat-exchange tubes located in the fluidisation zone for removing heat from the fluidisation zone and/or for providing heat to the fluidisation zone, said heat-exchange tubes being located longitudinally with respect to the axis of the fluidisation zone with a rectangular pitch, one side of which having a length at least one and a half times the length of the other side and/or with a triangular pitch, having two sides each at least one and a half times the length of the shortest side.

2. Apparatus as claimed in claim 1 in which the rectangular pitch of the heat-exchange tubes has sides of length x and y in which x is at least 2.5 times y.

3. Apparatus as claimed in claim 1 in which the triangular pitch arrangement has two sides each of which is at least 2.5 times the length of the shortest side.

4. Apparatus as claimed in claim 1 in which the heat exchange tubes have a diameter of 50 mm and the minimum distance between tubes is 25 mm, corresponding to a minimum distance between heat exchange tubes of 75 mm centre to centre.

5. Apparatus as claimed in claim 1 further comprising means for introducing liquid into the reactor as reactant and/or for the purpose of removing heat therefrom by evaporation of the liquid.

6. Apparatus for reacting at least one reactant with molecular oxygen-containing gas in the presence of a fluidised bed of catalyst which apparatus comprises a reactor having:

(a) means for fluidising a bed of fluidisable catalyst within a fluidisation zone in the reactor;

(b) means for introducing at least one reactant into the reactor;

(c) means for introducing a molecular oxygen-containing gas into a fluidised bed of catalyst in the fluidisation zone in the reactor and contacting the at least one reactant with the molecular oxygen-containing gas in the presence of the fluidised bed of catalyst in the fluidisation zone; and (d) heat-exchange tubes located in the fluidisation zone longitudinally with respect to the axis of the fluidisation zone with a rectangular pitch, one side of which having a length at least one and a half times the length of the other side and/or with a triangular pitch, having two sides each at least one and a half times the length of the shortest side.

7. Apparatus as claimed in claim 6 in which the rectangular pitch of the heat-exchange tubes has sides of length x and y in which x is at least 2.5 times y.

8. Apparatus as claimed in claim 6 in which the triangular pitch arrangement has two sides each of which is at least 2.5 times the length of the shortest side.

9. Apparatus as claimed in claim 6 in which the heat exchange tubes have a diameter of 50 mm and the minimum distance between tubes is 25 mm, corresponding to a minimum distance between heat exchange tubes of 75 mm centre to centre.

10. Apparatus as claimed in claim 6 further comprising means for introducing liquid into the reactor as reactant and/or for the purpose of removing heat therefrom by evaporation of the liquid.

11. A process for removing heat from a fluidised bed of material and/or supplying heat to a fluidised bed of material which process comprises (i) fluidising a bed of fluidisable material within a fluidisation zone in a vessel having means for supporting the fluidised bed of material; and (ii) removing heat from the fluidised bed of material and/or providing heat to the fluidised bed of material, by heat-exchange tubes located in the fluidisation zone longitudinally with respect to the axis of the fluidisation zone with a rectangular pitch, one side of which having a length at least one and a half times the length of the other side and/or with a triangular pitch, having two sides each at least one and a half times the length of the shortest side.

12. A process for reacting at least one reactant with molecular oxygen-containing gas in the presence of a fluidised bed of catalyst which process comprises:
(a) fluidising a bed of fluidisable catalyst within a fluidisation zone in a reactor having means for supporting the fluidised bed of catalyst;
(b) introducing at least one reactant into the reactor;
(c) introducing a molecular oxygen-containing gas into the fluidised bed of catalyst in the fluidisation zone in the reactor;
(d) contacting the at least one reactant with the molecular oxygen-containing gas in the presence of the fluidised bed of catalyst in the fluidisation zone; and
(e) removing at least part of the heat of reaction from the fluidisation zone by heat-exchange tubes located in the fluidisation zone longitudinally with respect to the axis of the fluidisation zone with a rectangular pitch, one side of which having a length at least one and a half times the length of the other side and/or with a triangular pitch, having two sides each at least one and a half times the length of the shortest side.

13. A process as claimed in claim 12 in which the reaction is selected from the group consisting of (a) the acetoxylation of olefins, (b) the oxidation of ethylene to acetic acid and/or the oxidation of ethane to ethylene and/or acetic acid, (c) the ammoxidation of propylene, propane or mixtures thereof to acrylonitrile and (d) the oxidation of C4's to maleic anhydride.

14. A process as claimed in claim 12 in which there is reacted ethylene, acetic acid and oxygen to produce vinyl acetate.

15. A process as claimed in claim 14 in which the temperature of the cooling tubes is no less than 110° C.

16. A process as claimed in claim 11 in which the rectangular pitch of the heat-exchange tubes has sides of length x and y in which x is at least 2.5 times y.

17. A process as claimed in claim 12 in which the rectangular pitch of the heat-exchange tubes has sides of length x and y in which x is at least 2.5 times y.

18. A process as claimed in claim 13 in which the rectangular pitch of the heat-exchange tubes has sides of length x and y in which x is at least 2.5 times y.

19. A process as claimed in claim 11 in which the triangular pitch arrangement has two sides each of which is at least 2.5 times the length of the shortest side.

20. A process as claimed in claim 12 in which the triangular pitch arrangement has two sides each of which is at least 2.5 times the length of the shortest side.

21. A process as claimed in claim 13 in which the triangular pitch arrangement has two sides each of which is at least 2.5 times the length of the shortest side.

22. A process as claimed in claim 11 in which the heat exchange tubes have a diameter of 50 mm and the minimum distance between tubes is 25 mm, corresponding to a minimum distance between heat exchange tubes of 75 mm centre to centre.

23. A process as claimed in claim 12 in which the heat exchange tubes have a diameter of 50 mm and the minimum distance between tubes is 25 mm, corresponding to a minimum distance between heat exchange tubes of 75 mm centre to centre.

24. A process as claimed in claim 11 in which the heat exchange tubes are operated at a temperature of not less than the dew point of the fluid in the fluidisation zone.

25. A process as claimed in claim 12 in which the heat exchange tubes are operated at a temperature of not less than the dew point of the fluid in the fluidisation zone.

26. A process as claimed in claim 13 in which the heat exchange tubes are operated at a temperature of not less than the dew point of the fluid in the fluidisation zone.

27. A process as claimed in claim 12 in which at least a part of the heat of reaction is removed from the reactor by introducing to the reactor cold gas and removing from the reactor hot gas.

28. A process as claimed in 12 in which liquid is introduced into the reactor as reactant and/or for the purpose of removing heat therefrom by evaporation of the liquid.

29. A process as claimed in 27 in which liquid is introduced into the reactor as reactant and/or for the purpose of removing heat therefrom by evaporation of the liquid.

30. A process as claimed in claim 29 in which 30 to 40% of the heat of reaction is removed by addition of liquid to the reactor, 30 to 40% of the heat of reaction is removed by recycle of cooled gas and 30 to 40% of the heat of reaction is removed by means of the heat exchange tubes.

31. A process as claimed in claim 11 in which the heat-exchange tubes are supplied with a heating fluid.

32. A process as claimed in claim 12 in which the heat exchange tubes are supplied with heating fluid to heat up the fluid bed reactor at start-up and when the reactor is at the required temperature the heating fluid is replaced by cooling fluid.

33. A process as claimed in claim 13 in which the heat exchange tubes are supplied with heating fluid to heat up the fluid bed reactor at start-up and when the reactor is at the required temperature the heating fluid is replaced by cooling fluid.

34. A process as claimed in claim 14 in which the temperature of the cooling tubes is at least 120° C.

35. A process as claimed in claim 11 in which the heat exchange tubes are operated at a temperature of at least 10° C. above the dew point of the fluid in the fludisation zone.

36. A process as claimed in claim 11 in which the heat exchange tubes are operated at a temperature 10 to 15° C. greater than the dew point of the fluid in the fluidisation zone.

37. A process as claimed in claim 12 in which the heat exchange tubes are operated at a temperature of at least 10° C. above the dew point of the fluid in the fluidisation zone.

38. A process as claimed in claim 12 in which the heat exchange tubes are operated at a temperature 10 to 15° C. greater than the dew point of the fluid in the fluidisation zone.

39. A process as claimed in claim 13 in which the heat exchange tubes are operated at a temperature at least 10° C. above the dew point of the fluid in the fluidisation zone.

40. A process as claimed in claim 13 in which the heat exchange tubes are operated at a temperature 10 to 15° C. greater than the dew point of the fluid in the fluidisation zone.

41. Apparatus comprising a vessel having:
(1) a fluidiser for fluidising a bed of fluidisable material within a fluidisation zone in the vessel; and
(2) heat-exchange tubes located in the fluidisation zone for removing heat from the fluidisation zone and/or for providing heat to the fluidisation zone, said heat-exchange tubes being located longitudinally with respect to the axis of the fluidisation zone with a rectangular pitch, one side of which having a length at least one and a half times the length of the other side and/or with a triangular pitch, having two sides each at least one and a half times the length of the shortest side.

* * * * *